United States Patent
Okada et al.

(10) Patent No.: US 12,099,072 B2
(45) Date of Patent: Sep. 24, 2024

(54) CELL PICKING DEVICE

(71) Applicant: SHIMADZU CORPORATION, Kyoto (JP)

(72) Inventors: Mika Okada, Kyoto (JP); Akari Takeda, Kyoto (JP); Yamato Maeda, Kyoto (JP); Yoshitake Yamamoto, Kyoto (JP); Potsun Chiang, Kyoto (JP); Yoshitaka Noda, Kyoto (JP); Takashi Inoue, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 0 days.

(21) Appl. No.: 17/628,029

(22) PCT Filed: Jul. 26, 2019

(86) PCT No.: PCT/JP2019/029512
§ 371 (c)(1),
(2) Date: Jan. 18, 2022

(87) PCT Pub. No.: WO2021/019622
PCT Pub. Date: Feb. 4, 2021

(65) Prior Publication Data
US 2022/0260605 A1    Aug. 18, 2022

(51) Int. Cl.
*G01N 35/10* (2006.01)
*B01L 3/02* (2006.01)
(Continued)

(52) U.S. Cl.
CPC ........ *G01N 35/1072* (2013.01); *B01L 3/0237* (2013.01); *B25J 9/1679* (2013.01);
(Continued)

(58) Field of Classification Search
None
See application file for complete search history.

(56) References Cited

U.S. PATENT DOCUMENTS

| | | | |
|---|---|---|---|
| 2007/0038411 A1* | 2/2007 | Taki | G01N 35/00722 |
| | | | 702/182 |
| 2013/0027539 A1* | 1/2013 | Kiyota | C12M 41/36 |
| | | | 348/79 |

(Continued)

FOREIGN PATENT DOCUMENTS

| | | |
|---|---|---|
| CN | 204602216 U | 9/2015 |
| CN | 109387512 A | 2/2019 |

(Continued)

OTHER PUBLICATIONS

Notification of Reasons for Refusal dated Dec. 20, 2022 from the Japanese Patent Office in Application No. 2021-536466.
(Continued)

*Primary Examiner* — P. Kathryn Wright
(74) *Attorney, Agent, or Firm* — Sughrue Mion, PLLC

(57) ABSTRACT

A cell picking device includes a stage, a sucker, a driver, a work content receiver, a registrar and a device controller. A sample container is placed on the stage. The driver is provided to execute sample scraping work and sample sucking work using a pipette tip attached to the sucker. In a case in which selection of work contents of the driver is received by the work content receiver, a work procedure including the received work contents of the driver is registered by the registrar. The work of the driver is controlled by the device controller in accordance with the registered work procedure.

8 Claims, 13 Drawing Sheets

(51) Int. Cl.
  *B25J 9/16* (2006.01)
  *C12M 1/00* (2006.01)
  *C12M 1/26* (2006.01)
  *G01N 35/00* (2006.01)

(52) U.S. Cl.
  CPC ........... *B25J 9/1682* (2013.01); *B25J 9/1697* (2013.01); *C12M 1/26* (2013.01); *C12M 33/00* (2013.01); *C12M 47/04* (2013.01); *G01N 35/00732* (2013.01); *G01N 35/1009* (2013.01); *G01N 2035/0091* (2013.01)

(56) References Cited

U.S. PATENT DOCUMENTS

| | | |
|---|---|---|
| 2016/0169775 A1 | 6/2016 | Kei et al. |
| 2017/0061078 A1* | 3/2017 | Natsume .......... G01N 35/00722 |
| 2017/0203290 A1 | 7/2017 | Ando et al. |
| 2018/0079999 A1 | 3/2018 | Blanchard |
| 2018/0087020 A1 | 3/2018 | Blanchard |
| 2018/0087021 A1 | 3/2018 | Blanchard |
| 2018/0119086 A1 | 5/2018 | Markussen et al. |
| 2018/0346868 A1 | 12/2018 | Blanchard |
| 2019/0031993 A1 | 1/2019 | Matsunaga et al. |
| 2019/0039070 A1 | 2/2019 | Matsunaga et al. |
| 2019/0049357 A1 | 2/2019 | Matsumoto et al. |
| 2020/0065363 A1* | 2/2020 | Yamane ................. G06F 40/174 |
| 2020/0248132 A1 | 8/2020 | Markussen et al. |
| 2020/0347339 A1 | 11/2020 | Blanchard |
| 2020/0377833 A1 | 12/2020 | Inoue et al. |
| 2021/0222110 A1 | 7/2021 | Blanchard |
| 2021/0261903 A1 | 8/2021 | Blanchard |
| 2022/0089997 A1 | 3/2022 | Blanchard |
| 2022/0243167 A1 | 8/2022 | Blanchard |
| 2022/0259546 A1 | 8/2022 | Blanchard |

FOREIGN PATENT DOCUMENTS

| | | | |
|---|---|---|---|
| JP | 2012208234 A | * | 10/2012 |
| JP | 2016-112012 A | | 6/2016 |
| JP | 2018-510659 A | | 4/2018 |
| WO | 2016/147239 A1 | | 9/2016 |
| WO | 2016/150446 A1 | | 9/2016 |
| WO | 2017/170993 A1 | | 10/2017 |
| WO | 2019/176093 A1 | | 9/2019 |

OTHER PUBLICATIONS

International Search Report for PCT/JP2019/029512, dated Oct. 15, 2019.
Written Opinion for PCT/JP2019/029512, dated Oct. 15, 2019.
International Search Report for corresponding Application No. PCT/JP2019/029513, mailed Oct. 21, 2019.
Written Opinion for corresponding Application No. PCT/JP2019/029513, mailed Oct. 21, 2019 (English machine translation).
Office Action in corresponding Chinese Patent Application No. 201980098273.5 dated Dec. 11, 2023, with English machine translation.
International Search Report with respect to International Patent Application No. PCT/JP2018/010488, mailed Jun. 19, 2018.
Written Opinion of the International Searching Authority with respect to International Patent Application No. PCT/JP2018/010488 (English Machine Translation), mailed Jun. 19, 2018.
Office Action for corresponding Chinese Patent Application No. 201880089296.5 dated Dec. 21, 2022, with English machine translation.
Practical Handbook of Middle School Chemistry Experiments, Education Science Press, p. 28, May 31, 1991, with partial English translation.
Notice of Decision of Refusal in corresponding Chinese Patent Application No. 201880089296.5 dated Mar. 31, 2023, with English machine translation.
Chinese Office Action issued Dec. 11, 2023 in Application No. 201980098792.1.

* cited by examiner

FIG. 7

| SCRAPING CONFIRMATION | DISCHARGE POSITION | PIPETTING | IMAGING | METHOD SAVING |

DO YOU WANT TO EXECUTE IMAGING AUTOMATICALLY?

- PRE-AND-POST SUCTION
- POST-SUCTION
- NO

METHOD NAME : ——
WORK MODE : PICKING MODE
SCRAPING CONFIRMATION : YES
DISCHARGE POSITION : IN-VIEW
ACCOMMODATING PLATE : ——
PIPETTING : 3
IMAGING :

CANCEL

CELL PICKING DEVICE

CROSS REFERENCE TO RELATED APPLICATIONS

This application is a National Stage of International Application No. PCT/JP2019/029512 filed Jul. 26, 2019.

TECHNICAL FIELD

The present invention relates to a cell picking device.

BACKGROUND ART

In a case in which specific cells are to be sucked from a container such as a cell culture container, a worker sucks the cells manually using a suction tool such as a pipette while checking the position of the subject cells with a microscope. Further, since such work requires a skill, a cell-sucking system that assists cell-sucking work has been suggested for an unskilled worker (see Patent Document 1, for example.)

In the cell-sucking system described in Patent Document 1, a tubular tip for sucking cells contained in a container is attached to a sucker. The end of the tip is detected optically by a detector, and the sucker is moved three-dimensionally by a transporter such that the end of the tip is guided into specific cells based on its detection result.

[Patent Document 1] JP 2016-112012 A

SUMMARY OF INVENTION

Technical Problem

In a cell picking device, various constituent elements such as a tip need to be operated to meet requirements of a worker such as purpose, efficiency, reliability or the like in regard to cell suction. In a case in which the worker is skilled, it is possible to operate the cell picking device in accordance with appropriate work contents based on experience or intuition. However, in a case in which the worker is not skilled, it is difficult to operate the cell picking device in accordance with appropriate work contents. As such, it is desirable to develop a cell picking device with improved operability.

An object of the present invention is to provide a cell picking device with improved operability.

Solution to Problem

An aspect according to the present invention relates to a cell picking device for sucking cells from a liquid sample in a sample container, that includes a stage on which the sample container is placeable, a sucker to which a pipette tip is attachable, a driver that drives the sucker to execute sample scraping work and drives the sucker to execute sample sucking work, using the pipette tip, a work content receiver that receives selection of work contents of the driver, a registrar that registers a work procedure including work contents of the driver received by the work content receiver, and a device controller that controls work of the driver in accordance with a work procedure registered by the registrar.

Advantageous Effects of Invention

The present invention enables improvement of operability of a cell picking device.

BRIEF DESCRIPTION OF THE DRAWINGS

FIG. 7 is a diagram showing one example of the plurality of selection screens to be sequentially displayed in the display unit of FIG. 1.

DESCRIPTION OF EMBODIMENTS

(1) Configuration of Cell Picking Device

Figure 1:
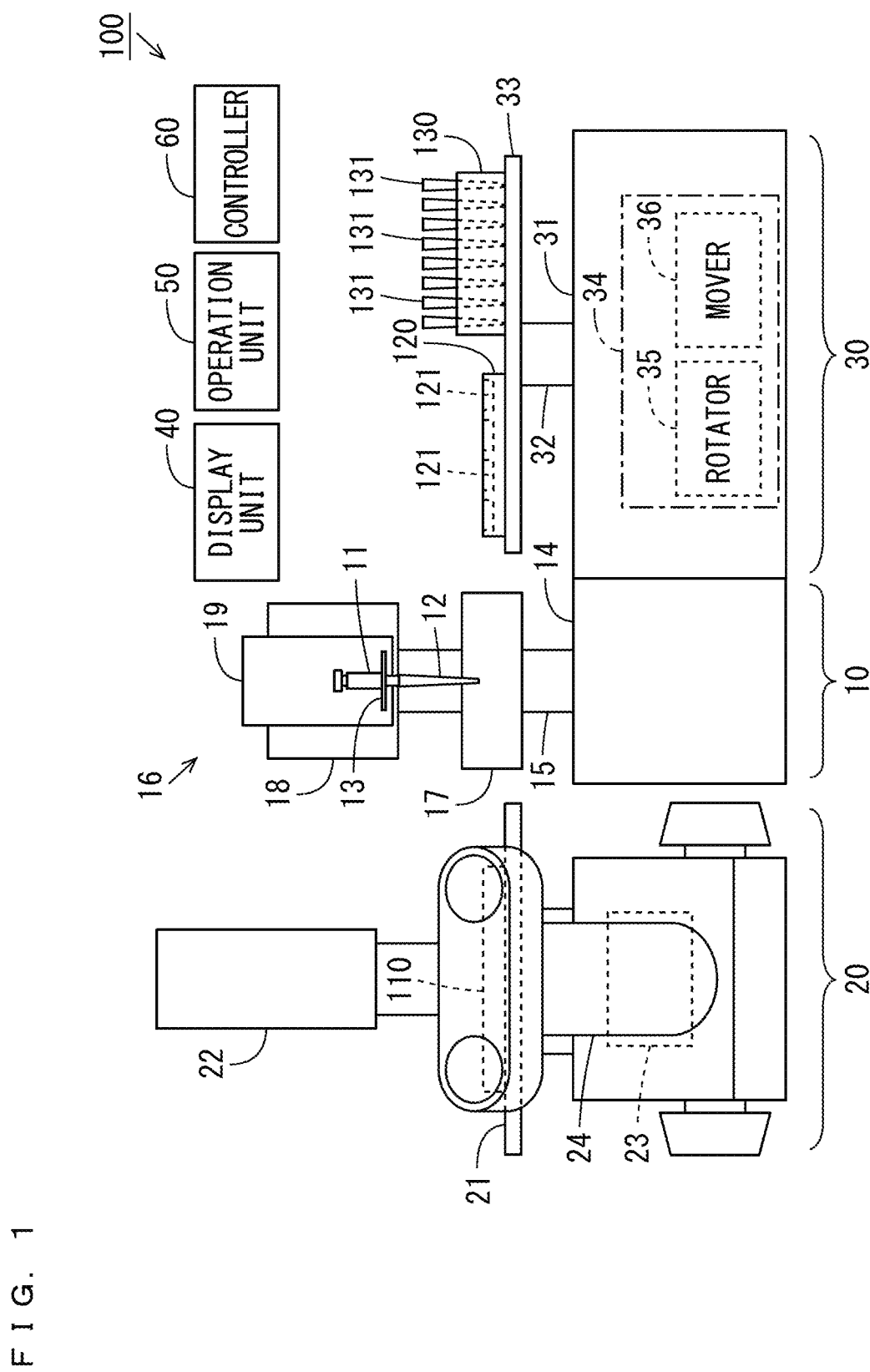
FIG. 1 is a schematic diagram showing the configuration of a cell picking device according to one embodiment of the present invention.

A cell picking device according to embodiments of the present invention will be described below in detail with reference to the drawings. FIG. 1 is a schematic diagram showing the configuration of the cell picking device according to one embodiment of the present invention. As shown in FIG. 1, the cell picking device 100 includes a suction device 10, an observation device 20, a plate changer 30, a display unit 40, an operation unit 50 and a controller 60. Further, the cell picking device 100 is provided with a sample container 110, an accommodating plate 120 and a pipette tip rack 130 (hereinafter simply referred to as a rack 130.)

The sample container 110 is a petri plate, for example, and accommodates a sample including cells. The accommodating plate 120 is a multi-well plate in which a plurality of wells 121 are arranged and used for culturing of cells. The rack 130 holds a plurality of replacement pipette tips 131 (hereinafter simply referred to as replacement tips 131.) In the present example, 24 wells 121 are arranged in 4 rows by 6 columns in the accommodating plate 120. Further, 96 replacement tips 131 are held while being arranged in 8 rows by 12 columns in the rack 130.

The suction device 10 includes a sucker 11, a pipette tip 12 (hereinafter simply referred to as a tip 12,) a holder 13, a base 14, a vertical shaft 15 and a driver 16. The driver 16 includes rotators 17, 18 and a suction driver 19. The sucker 11 is a pipette-shape arm. The tip 12 is attached to the end of the sucker 11. Any replacement tip 131 held in the rack 130 can be attached to the end of the sucker 11 as the tip 12.

The holder 13 holds the sucker 11 at the suction driver 19. The vertical shaft 15 is provided on the upper surface of the base 14 to extend in an up-and-down direction. The rotator 17 includes an electric motor, for example, and is attached to the upper end of the vertical shaft 15 to be rotatable in a horizontal plane. The rotator 18 includes an electric motor, for example, and is attached to the rotator 17 to be rotatable in a vertical plane. The rotator 17 and the rotator 18 may be constituted by a single electric motor, etc. which is rotatable in the horizontal plane and the vertical plane.

The suction driver 19 includes a stepping motor, for example, and is attached to the rotator 18 to be advanceable and retreatable in a predetermined direction (the up-and-down direction in a case in which the rotator 18 is not rotating in the vertical plane). Further, the suction driver 19 includes a suction mechanism and is configured to be capable of sucking and discharging cells using the sucker 11. Further, the suction driver 19 includes a tip removal mechanism and is configured to be capable of removing the tip 12 from the end of the sucker 11.

The driver 16 can scrape off cells in the sample container 110 using the end of the tip 12 and can suck the scraped cells into the tip 12 through the sucker 11. Further, the driver 16 can discharge (seed) cells that have been sucked into the tip 12 through the sucker 11 into any well 121 of the accommodating plate 120.

The observation device 20 includes a stage 21, an illuminator 22, an imager 23 and a microscope 24 and is arranged to be adjacent to the suction device 10. The sample container 110 is placed on the stage 21. The illuminator 22 is arranged above the stage 21. The illuminator 22 includes a light source such as a light emitting diode, for example, and illuminates the sample container 110 placed on the stage 21. The stage 21 is translucent. Alternatively, an opening through which light from the illuminator 22 passes downwardly may be formed in the stage 21.

The imager 23 is arranged below the stage 21. The imager 23 includes a plurality of lenses, a camera and so on, and picks up an image while magnifying a sample in the sample container 110 illuminated by the illuminator 22. The microscope 24 includes an eyepiece, a lens-barrel, an objective lens, etc., and is used by a user when a sample in the sample container 110 placed on the stage 21 is magnified for observation.

The plate changer 30 is an optional device arranged to be opposite to the observation device 20 with the suction device 10 provided therebetween and is configured to be attachable to and detachable from the suction device 10. The plate changer 30 includes a base 31, a vertical shaft 32, a platform 33 and a driver 34. The vertical shaft 32 is provided to extend in the up-and-down direction in the base 31. An upper portion of the vertical shaft 32 projects from the base 31. The platform 33 is attached to the upper end of the vertical shaft 32 in a horizontal attitude. The accommodating plate 120 and the rack 130 are placed on the platform 33.

The driver 34 includes a rotator 35 and a mover 36 and is connected to the platform 33 through the vertical shaft 32 in the base 31. The rotator 35 includes an electric motor, for example, and rotates the platform 33 in a horizontal plane.

Thus, the accommodating plate 120 and the rack 130 placed on the platform 33 are selectively moved to the vicinity of the suction device 10.

Specifically, when the suction device 10 discharges cells into any well 121, the accommodating plate 120 is moved to the vicinity of the suction device 10. On the other hand, when any replacement tip 131 is attached to the sucker 11, the rack 130 is moved to the vicinity of the suction device 10. With this configuration, an increase in moving range of the platform 33 is prevented.

The mover 36 includes a stepping motor, for example, and moves the platform 33 horizontally in a horizontal plane. Specifically, the mover 36 moves any well 121 of the accommodating plate 120 or any replacement tip 131 in the rack 130 to a position accessible by the sucker 11 (below the sucker 11, for example). Thus, cells can be discharged from the suction device 10 into the well 121 or the replacement tip 131 can be attached to the sucker 11.

The display unit 40 includes an LCD (Liquid Crystal Display) panel or an organic EL (Electroluminescence) panel, for example. The display unit 40 sequentially displays a plurality of GUIs (Graphical User Interfaces) for receiving selection of work contents of the suction device 10, the observation device 20 and the plate changer 30 as selection screens. Further, the display unit 40 displays a work screen for receiving an instruction during work of the cell picking device 100.

The operation unit 50 includes a keyboard, a pointing device, etc. As a pointing device, a mouse, a joy stick or the like is used. The display unit 40 and the operation unit 50 may be integrally constituted by a touch panel display. The user can operate a button, a pull-down menu or the like in a selection screen or a work screen displayed in the display unit 40 using the operation unit 50.

The controller 60 includes a personal computer, for example, and includes a CPU (Central Processing Unit), a memory and so on. The controller 60 registers a work procedure including the work contents received by a selection screen and controls the work of the suction device 10, the observation device 20 and the plate changer 30 in accordance with the registered work procedure.

(2) Selection Screens

FIGS. 2 to 8 are diagrams showing one example of a plurality of selection screens to be sequentially displayed in the display unit 40 of FIG. 1. As shown in FIGS. 2 to 8, each selection screen includes a step display region 1 and a GUI display region 2. In the step display region 1, a selected step name and so on are displayed. In the GUI display region 2, buttons, pull-down menus and so on used for selecting the work contents of the suction device 10, the observation device 20 and the plate changer 30 are displayed. Details of each selection screen will be described below.

(a) Method Selection Screen

Figure 2:
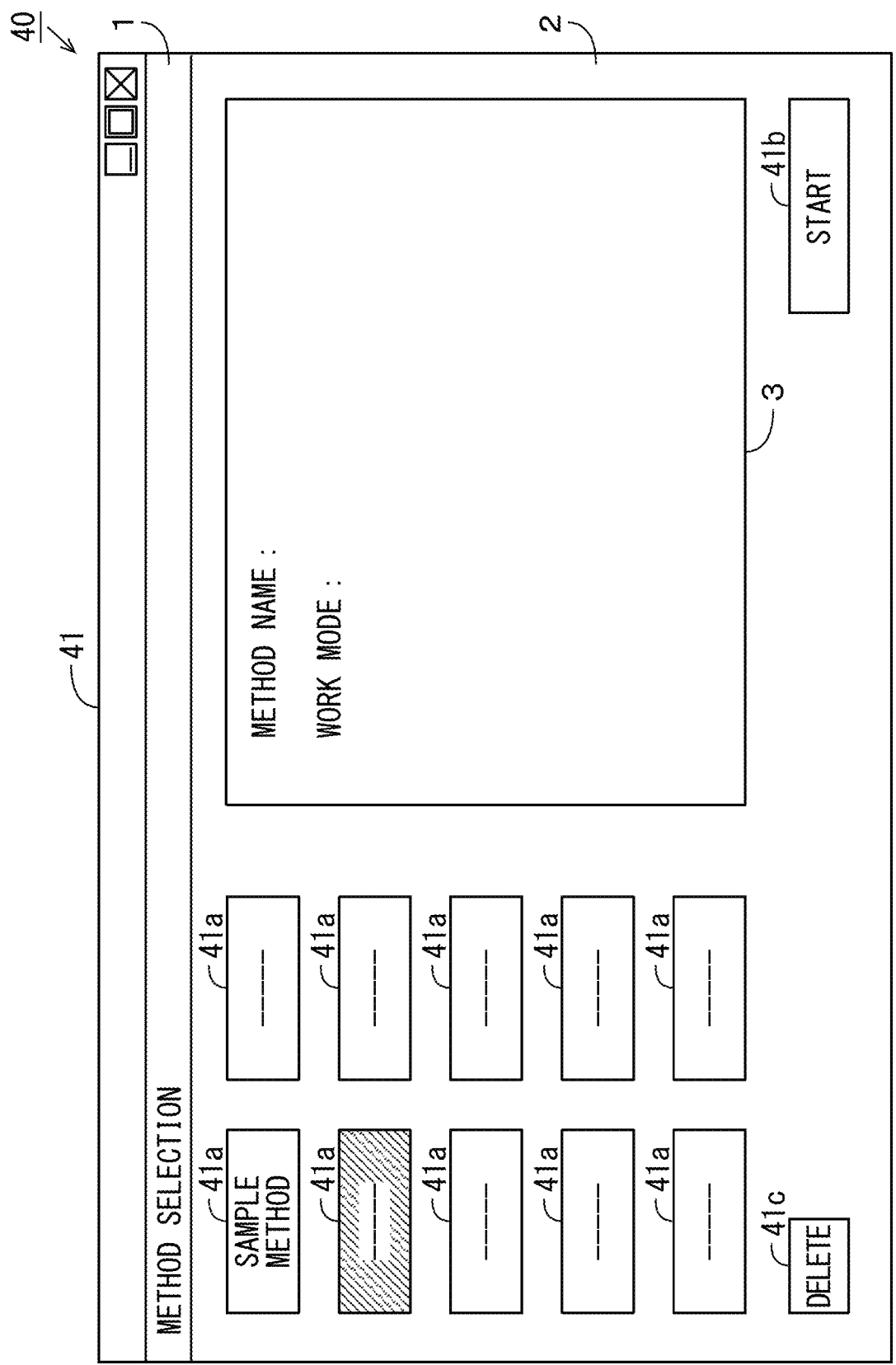
FIG. 2 is a diagram showing one example of a plurality of selection screens to be sequentially displayed in a display unit of FIG. 1.

The selection screen of FIG. 2 is referred to as a method selection screen 41. As shown in FIG. 2, in the method selection screen 41, a step name "METHOD SELECTION" is displayed in the step display region 1. Further, in the GUI display region 2, a plurality of method selection buttons 41*a*, a start button 41*b* and a delete button 41*c* are displayed, and a work content field 3 is displayed.

Each method selection button 41*a* is operated in a case in which a work procedure (hereinafter referred to as a method) of the suction device 10, the observation device 20 and the plate changer 30 is newly created. Further, in a case in which a method is created by an operation of any of the method selection buttons 41a, the name of the method (hereinafter referred to as a method name) is displayed in the method selection button 41a. In the example of FIG. 2, the method name "SAMPLE METHOD" is displayed in the method selection button 41a.

In the method selection screen 41, the operated method selection button 41a is highlighted so as to be identifiable. In the example of FIG. 2, the selected method selection button 41a is highlighted by a hatching pattern. Further, in the work content field 3, the name of a method corresponding to an operated method selection button 41a and the work contents included in the method are displayed.

In the present example, a method selection button 41a a method name of which is not displayed, that is, a method selection button 41a which is not used for creation of a method is selected. In this case, the work contents and the like of the method are not displayed in the work content field 3. When the start button 41b is operated in this state, the display in the display unit 40 is switched from the method selection screen 41 to a selection screen of FIG. 3 corresponding to the next step.

On the other hand, in a case in which the start button 41b is operated with a method selection button 41a displaying a method name selected, the method corresponding to the method selection button 41a is selected by the controller 60 of FIG. 1. The work of the cell picking device 100 is controlled in accordance with the selected method. In a case in which the delete button 41c is operated with a method selection button 41a displaying a method name selected, the method corresponding to the method selection button 41a is deleted.

(b) Work Mode Selection Screen

Figure 3:
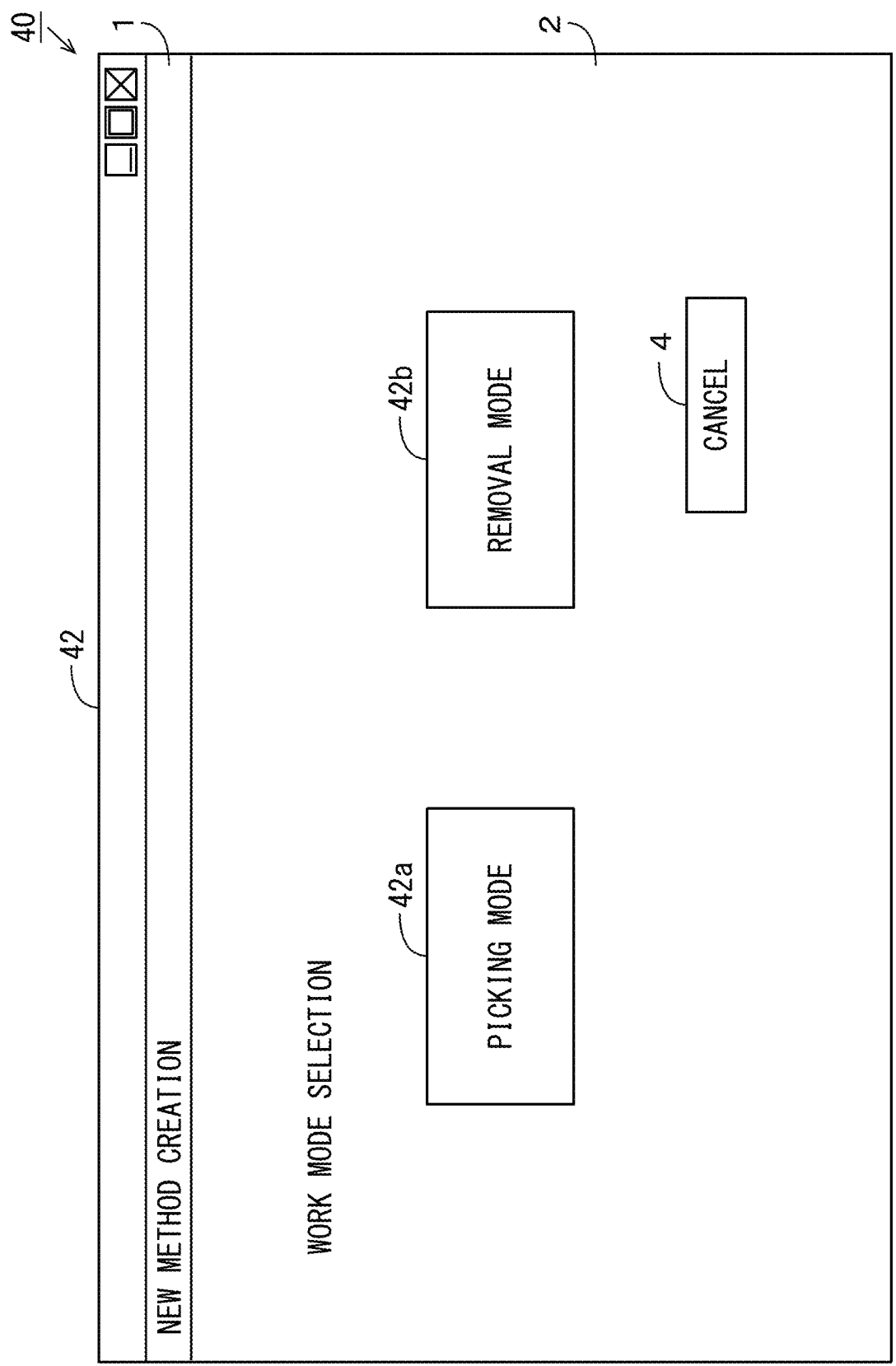
FIG. 3 is a diagram showing one example of the plurality of selection screens to be sequentially displayed in the display unit of FIG. 1.

The selection screen of FIG. 3 is referred to as a work mode selection screen 42. As shown in FIG. 3, in the work mode selection screen 42, the step name "NEW METHOD CREATION" is displayed in the step display region 1. Further, in the GUI display region 2, a picking mode button 42a and a removal mode button 42b are displayed, and a cancel button 4 is also displayed.

Here, selection of work contents of the suction device 10 and the plate changer 30 includes selection of a work mode, and a user can select a picking mode or a removal mode as the work mode. The picking mode is a work mode in which the tip 12 of FIG. 1 scrapes and sucks cells from the sample container 110 and discharges the sucked cells to any of the wells 121 of the accommodating plate 120. The removal mode is a work mode in which the tip 12 removes cells by scraping and sucking cells from the sample container 110.

In a case in which the picking mode is selected as the work mode, the picking mode button 42a is operated. In this case, the display in the display unit 40 is switched from the work mode selection screen 42 to the selection screen of FIG. 4 corresponding to the next step. In the present example, the picking mode is selected. On the other hand, in a case in which the removal mode is selected as the work mode, the removal mode button 42b is operated. In this case, the display in the display unit 40 is switched from the work mode selection screen 42 to the selection screen of FIG. 7 corresponding to the subsequent step.

In a case in which the cancel button 4 is operated, the selection screen displayed in the display unit 40 returns to the method selection screen 41 of FIG. 2. The same applies to a case in which the cancel button 4 in each of FIGS. 4 to 8 is operated.

Further, in a case in which the picking mode is selected, a picking capacity indicating a capacity of the sucker to pick cells and/or a picking speed may further be displayed. Here, the picking capacity includes the options of "small," "medium" and "large." Further, the picking speed is a suction speed and/or a moving speed of the tip 12 and includes the options of "slow," "medium" and "fast." These options are selectable by a user operation.

(c) Scraping Confirmation Selection Screen

Figure 4:
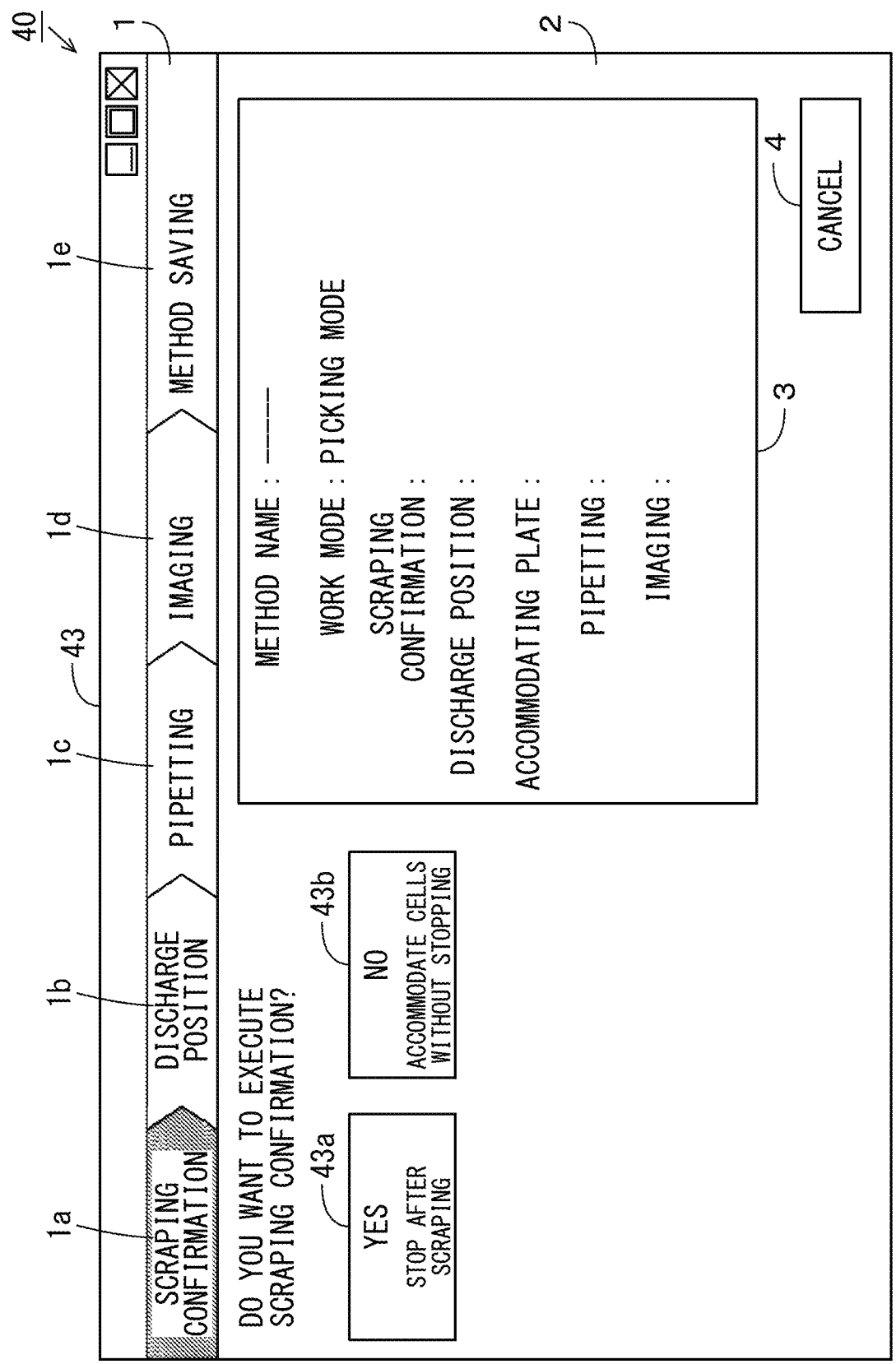
FIG. 4 is a diagram showing one example of the plurality of selection screens to be sequentially displayed in the display unit of FIG. 1.

The selection screen of FIG. 4 is referred to as a scraping confirmation selection screen 43. As shown in FIG. 4, in the scraping confirmation selection screen 43, a plurality of step indexes 1a to 1e respectively corresponding to a plurality of steps are displayed in the step display region 1. In the plurality of step indexes 1a to 1e, corresponding step names are displayed. The plurality of step indexes 1a to 1e are arranged in a left-and-right direction in a breadcrumb navigation, and the step index corresponding to a current step is highlighted so as to be identifiable.

In the example of FIG. 4, the step names "SCRAPING CONFIRMATION," "DISCHARGE POSITION," "PIPETTING," "IMAGING" and "METHOD SAVING" are displayed in the step indexes 1a to 1e, respectively. Further, the step index 1a (step name "SCRAPING INFORMATION") corresponding to the current step is highlighted by a hatching pattern. The step indexes 1a to 1e are also displayed in the step display region 1 in the selection screen of each of FIGS. 5 to 8.

In the GUI display region 2, a YES button 43a and a NO button 43b are displayed, and the work content field 3 and the cancel button 4 are displayed. In the present example, because the picking mode is selected as the work mode of the cell picking device 100, "PICKING MODE" is displayed in the work content field 3 as the work mode included in the method.

Here, selection of the work contents of the suction device 10 includes selection of whether to execute scraping confirmation. In the picking mode, the user can select whether to execute cell-scraping confirmation. In a case in which wishing to reliably suck relatively large cells, the user may select to execute scraping confirmation. Further, in a case in which cells are relatively small or a case in which the user wishes to end work in a short period of time, the user may select not to execute scraping confirmation.

In a case in which the user selects to execute scraping confirmation, the YES button 43a is operated. In the present example, the user performs an operation to select execution of scraping confirmation. On the other hand, in a case in which the user selects not to execute scraping confirmation, the NO button 43b is operated. Regardless of whether the YES button 43a or the NO button 43b is operated, the display in the display unit 40 is switched from the scraping confirmation selection screen 43 to the selection screen of FIG. 5 corresponding to the next step.

(d) Discharge Position Selection Screen

Figure 5:
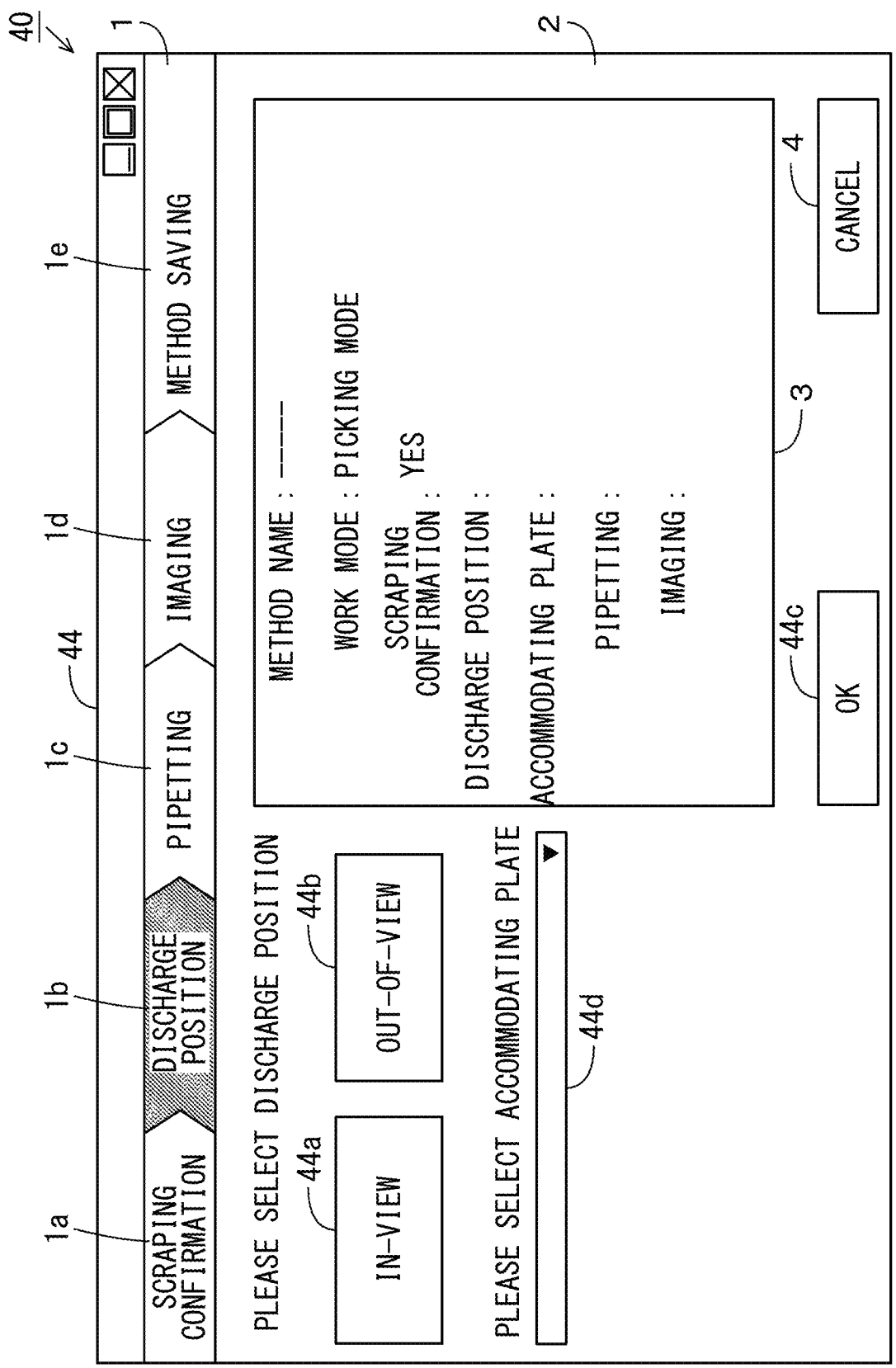
FIG. 5 is a diagram showing one example of the plurality of selection screens to be sequentially displayed in the display unit of FIG. 1

The selection screen of FIG. 5 is referred to as a discharge position selection screen 44. As shown in FIG. 5, in the discharge position selection screen 44, the plurality of step indexes 1a to 1e are displayed in the step display region 1, and the step index 1b (the step name "DISCHARGE POSITION") corresponding to the current step is highlighted by the hatching pattern.

In the GUI display region 2, an in-view button 44a, an out-of-view button 44b and an OK button 44c are displayed, and the work content field 3 and the cancel button 4 are displayed. In the present example, because execution of scraping confirmation is selected, "YES" is further displayed in the work content field 3 in regard to selection of whether to execute scraping confirmation included in the method.

Here, selection of the work contents of the suction device 10 and the plate changer 30 includes selection of a cell-discharge position, and the user can select in-view or out-of-view of the microscope 24 of FIG. 1 as a discharge position. In-view indicates a substantially central portion of the stage 21 (FIG. 1), for example. In a case in which the plate changer 30 (FIG. 1) is attached to the suction device 10 (FIG. 1), out-of-view indicates a predetermined position on the platform 33 (FIG. 1) of the plate changer 30. In a case in which the plate changer 30 is not attached to the suction device 10, out-of-view indicates a predetermined position on the base 14 (FIG. 1) of the suction device 10, for example.

In a case in which wishing to observe suction and discharging of cells under magnification using the microscope 24 while replacing the sample container 110 with a default accommodating plate 120, the user may select in-view. Further, in a case in which not needing to observe suction and discharging of cells under magnification, the user may select out-of-view. In this case, any of a variety of plate members can be used as the accommodating plate 120.

In a case in which in-view is selected, the in-view button 44a is operated. Thus, the OK button 44c becomes operable. In the present example, in-view is selected. On the other hand, in a case in which out-of-view is selected, the out-of-view button 44b is operated. In a case in which out-of-view is selected, an accommodating plate 120 used for discharging of cells is further selected. Specifically, in a case in which out-of-view is selected, a pull-down menu 44d for selecting identification information such as a name or a model number of the accommodating plate 120 is further displayed in the GUI display region 2. When the identification information is selected from the pull-down menu 44d, the OK button 44c becomes operable.

Figure 6:
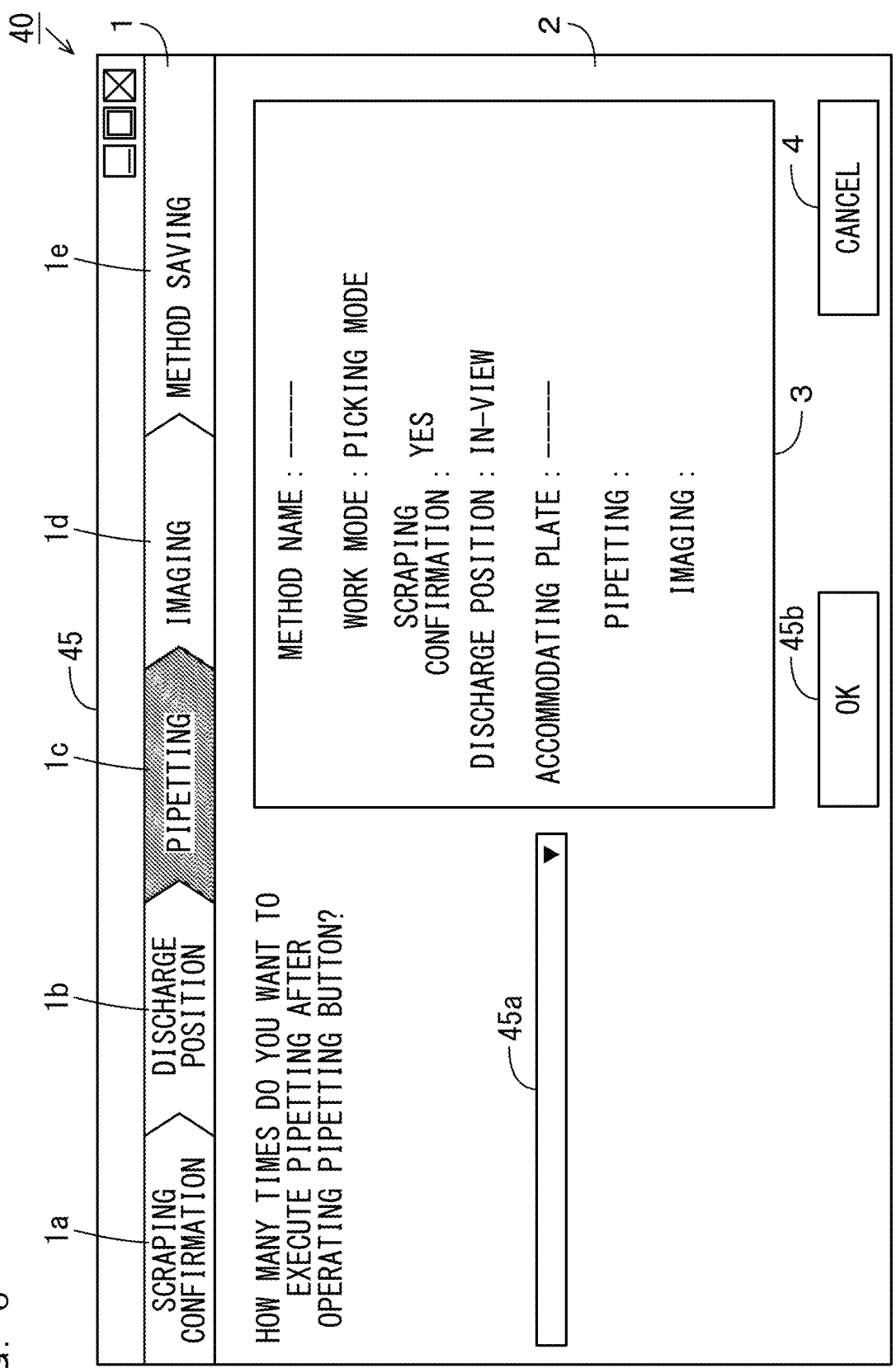
FIG. 6 is a diagram showing one example of the plurality of selection screens to be sequentially displayed in the display unit of FIG. 1

Regardless of whether in-view or out-of view is selected, when the OK button 44c is operated, the display in the display unit 40 is switched from the discharge position selection screen 44 to the selection screen of FIG. 6 corresponding to the next step.

(e) Pipetting Selection Screen

The selection screen of FIG. 6 is referred to as a pipetting selection screen 45. As shown in FIG. 6, in the pipetting selection screen 45, the plurality of step indexes 1a to 1e are displayed in the step display region 1, and the step index 1c (the step name "PIPETTING") corresponding to the current step is highlighted by the hatching pattern.

In the GUI display region 2, a pull-down menu 45a and an OK button 45b are displayed, and the work content field 3 and the cancel button 4 are displayed. In the present example, because in-view is selected as the discharge position, "IN-VIEW" is further displayed in the work content field 3 as the discharge position included in the method. In addition, in a case in which in-view is selected as the discharge position, because the accommodating plate 120 is not selected, the identification information of the accommodating plate 120 is not displayed in the work content field 3.

Here, selection of the work contents of the suction device 10 includes selection of a pipetting count in a case in which a pipetting button 48d of FIG. 9, described below, is operated. It is possible to separate a mass of cells sucked into the tip 12 and accommodate the leveled cells in a well 121 of the accommodating plate 120 by execution of pipetting.

1, 2 or 3 can be selected as a pipetting count from the pull-down menu 45a. In the present example, 3 is selected as the pipetting count. When the pipetting count is selected from the pull-down menu 45a, the OK button 45b becomes operable. In a case in which the OK button 45b is operated, the display in the display unit 40 is switched from the pipetting selection screen 45 to the selection screen of FIG. 7 corresponding to the next step.

(f) Imaging Selection Screen

The selection screen of FIG. 7 is referred to as an imaging selection screen 46. As shown in FIG. 7, in the imaging selection screen 46, the plurality of step indexes 1a to 1e are displayed in the step display region 1, and the step indicator 1d (the step name "IMAGING") corresponding to the current step is highlighted by the hatching pattern.

In the GUI display region 2, a pre-and-post suction button 46a, a post-suction button 46b, and a NO button 46c are displayed, and the work content field 3 and the cancel button 4 are displayed. In the present example, because 3 is selected as the pipetting count, "3" is further displayed in the work content field 3 as the pipetting count included in the method.

Here, selection of the work contents of the observation device 20 includes selection of whether to automatically execute imaging. In either one of the picking mode and the removal mode, the user can select whether to automatically execute imaging before and after suction of cells, automatically execute imaging only after suction of cells or not to automatically execute imaging. An image acquired by imaging is saved in a memory of the controller 60 of FIG. 1, for example.

In a case in which wishing to confirm whether cells have been sucked, the user may select to execute imaging before and after suction of cells. Further, in a case in which wishing to confirm whether cells have been removed, the user may select to execute imaging only after suction of cells. Further, in a case in which wishing to end work in a short period of time, the user may select not to execute imaging.

In a case in which the user selects to execute imaging before and after suction of cells, the pre-and-post suction button 46a is operated. In the present example, it is selected that imaging is executed before and after suction of cells. In a case in which it is selected that imaging is executed only after suction of cells, the post-suction button 46b is operated. In a case in which it is selected that imaging is not executed, the NO button 46c is operated. Regardless of whether any of the pre-and-post suction button 46a, the post-suction button 46b and the NO button 46c is operated, the display in the display unit 40 is switched from the imaging selection screen 46 to the selection screen of FIG. 8 corresponding to the next step.

(g) Method Saving Screen

Figure 8:
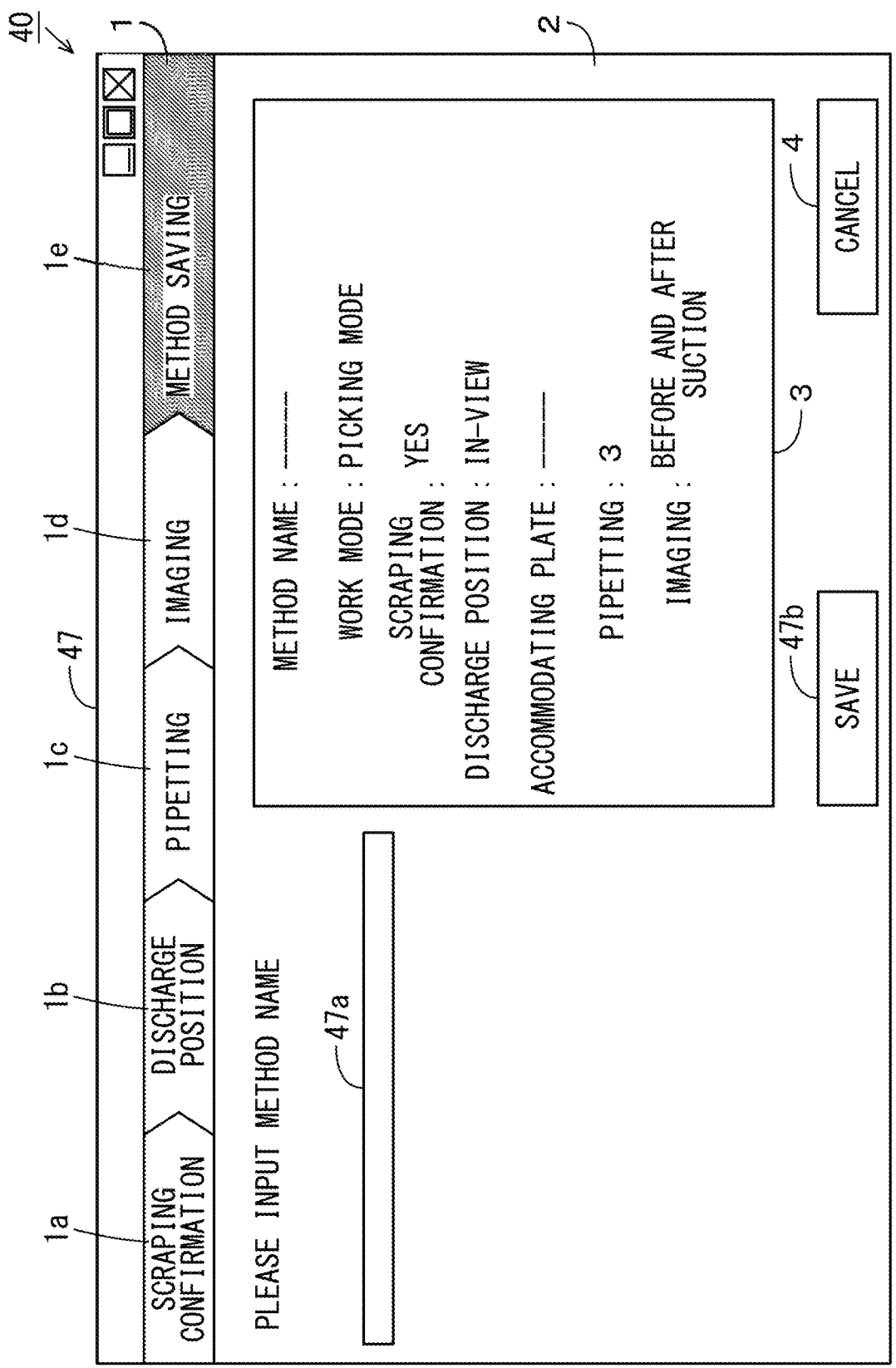
FIG. 8 is a diagram showing one example of the plurality of selection screens to be sequentially displayed in the display unit of FIG. 1

The selection screen of FIG. 8 is referred to as a method saving screen 47. As shown in FIG. 8, in the method saving screen 47, the plurality of step indexes 1a to 1e are displayed in the step display region 1, and the step index 1e (the step name "METHOD SAVING") corresponding to the current step is highlighted by the hatching pattern.

In the GUI display region 2, a method name input field 47a and a save button 47b are displayed, and the work content field 3 and the cancel button 4 are displayed. In the present example, because it is selected that imaging is executed before and after suction of cells, execution of imaging "BEFORE AND AFTER SUCTION" is further displayed in the work content field 3 in regard to selection of whether to execute imaging included in the method.

In the method name input field 47a, the name of a method including a plurality of selected work contents is input. When the method name is input in the method name input field 47a, the save button 47b becomes operable. When the save button 47b is operated, the method is saved and registered. In this case, the method name that is input in the method name input field 47a is displayed in the method selection button 41a of FIG. 2 to which the hatching pattern is applied.

(3) Work Screen

As described above, in the method selection screen 41 of FIG. 2, a method is selected when the start button 41b is operated with the method selection button 41a displaying the method name selected. Further, the work screen corresponding to a selected method is displayed in the display unit 40. Therefore, the user can select a desired work procedure included in a plurality of registered methods and cause the cell picking device 100 to work in accordance with the selected method. In the present example, the method including the work contents selected in the selection screens of FIGS. 2 to 8 is selected.

Figure 9:
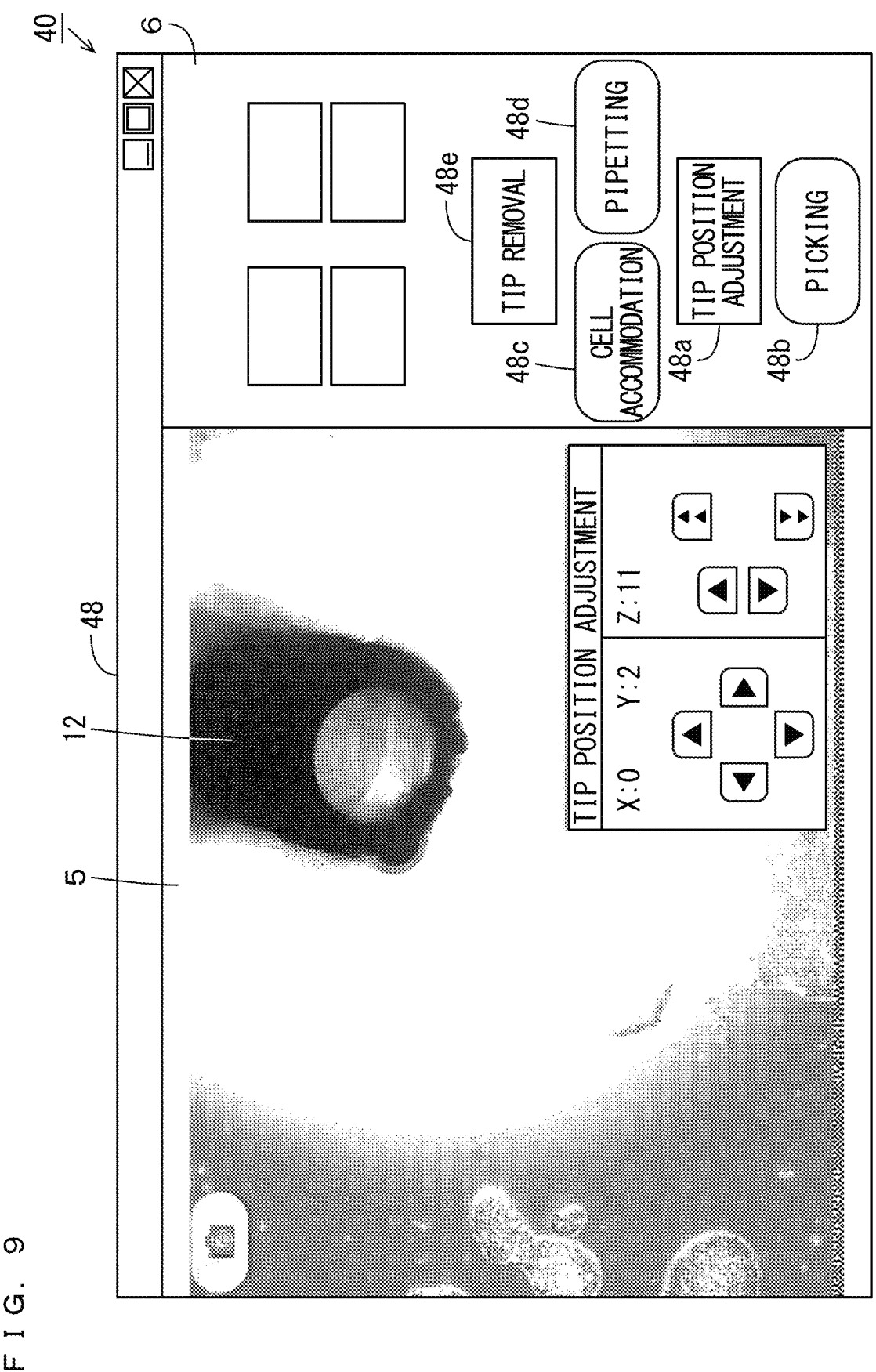
FIG. 9 is a diagram showing one example of a work screen displayed in the display unit of FIG. 1.

FIG. 9 is a diagram showing one example of a work screen displayed in the display unit 40 of FIG. 1. As shown in FIG. 9, the work screen 48 includes an image display region 5 and a GUI display region 6. An image observed with use of the microscope 24 of FIG. 1 is displayed in the image display region 5. The image displayed in the image display region 5 of FIG. 9 includes the end of the tip 12. Thus, the user can confirm the position of the end of the tip 12.

In the GUI display region 6, a tip position adjustment button 48a, a picking button 48b, a cell accommodation button 48c, the pipetting button 48d, a tip removing button 48e and so on are displayed. The tip position adjustment button 48a is operated when the position of the tip 12 is adjusted. In the present example, in a case in which the tip position adjustment button 48a is operated, an operation window for receiving an instruction for moving the tip 12 is further displayed in the work screen 48.

The picking button 48b is operated when the work for scraping cells in a sample using the tip 12 is started. In the present example, because the picking mode is selected, "PICKING" is displayed in the picking button 48b. However, in a case in which the removal mode is selected, "REMOVAL" is displayed in the picking button 48b. Also in the removal mode, the picking button 48b is operated when the scraping work is executed.

In the present example, because execution of cell-scraping confirmation is selected, driving of the sucker 11 is stopped after the scraping work is executed every time the picking button 48b is operated. Therefore, the user can repeat the scraping work by repeating to operate the picking button 48b. Further, after execution of the scraping work, the user can confirm whether cells have been appropriately scraped using the microscope 24.

On the other hand, in a case in which non-execution of cell-scraping confirmation is selected, the picking button 48b is allowed to be operated only once. In a case in which the picking button 48b is operated, the scraping work is executed, and then the cell-scraping work is executed without stopping of driving of the sucker 11.

The cell accommodation button 48c is operated when the cell sucking work with use of the tip 12 is executed. After the sucking work is executed, the tip 12 is retracted upwardly. In addition, in a case in which non-execution of cell-scraping confirmation is selected, because the sucking work is executed automatically, the cell accommodation button 48c becomes inoperable. In the present example, an image of a sample is picked up by the imager 23 of FIG. 1 before and after suction. Thus, an image representing whether cells in the sample have been sucked by the tip 12 is acquired and saved.

Further, because in-view is selected as the discharge position in the present example, after the sucking work is executed, a dialog window for confirming whether the accommodating plate 120 is placed on the stage 21 of FIG. 1 is displayed. The user can place the accommodating plate 120 on the stage 21 instead of the sample container 110 and position a desired well 121 of the accommodating plate 120 below the tip 12. Thereafter, it is notified in the dialog window that the accommodating plate 120 has been placed, so that the sucked cells are discharged and accommodated in the above-mentioned well 121.

On the other hand, in a case in which out-of-view is selected as the discharge position, the cells sucked into the tip 12 are automatically discharged to a predetermined well 121 of the accommodating plate 120 placed on the plate changer 30 of FIG. 1. The order of wells 121 to which cells are discharged is registered in advance in the controller 60.

The pipetting button 48d is operated when pipetting is executed. In the present example, because 3 is selected as a pipetting count, pipetting is executed 3 times by an operation of the pipetting button 48d. In a case in which pipetting is not executed, the user does not need to operate the pipetting button 48d.

The tip removing button 48e is operated when the tip 12 is removed from the sucker 11. In this case, any of the replacement tips 131 held in the rack 130 of FIG. 1 may be attached to the sucker 11 as a new tip 12. The order of attachment of the replacement tips 131 to the sucker 11 is registered in advance in the controller 60.

(4) Controller

Figure 10:
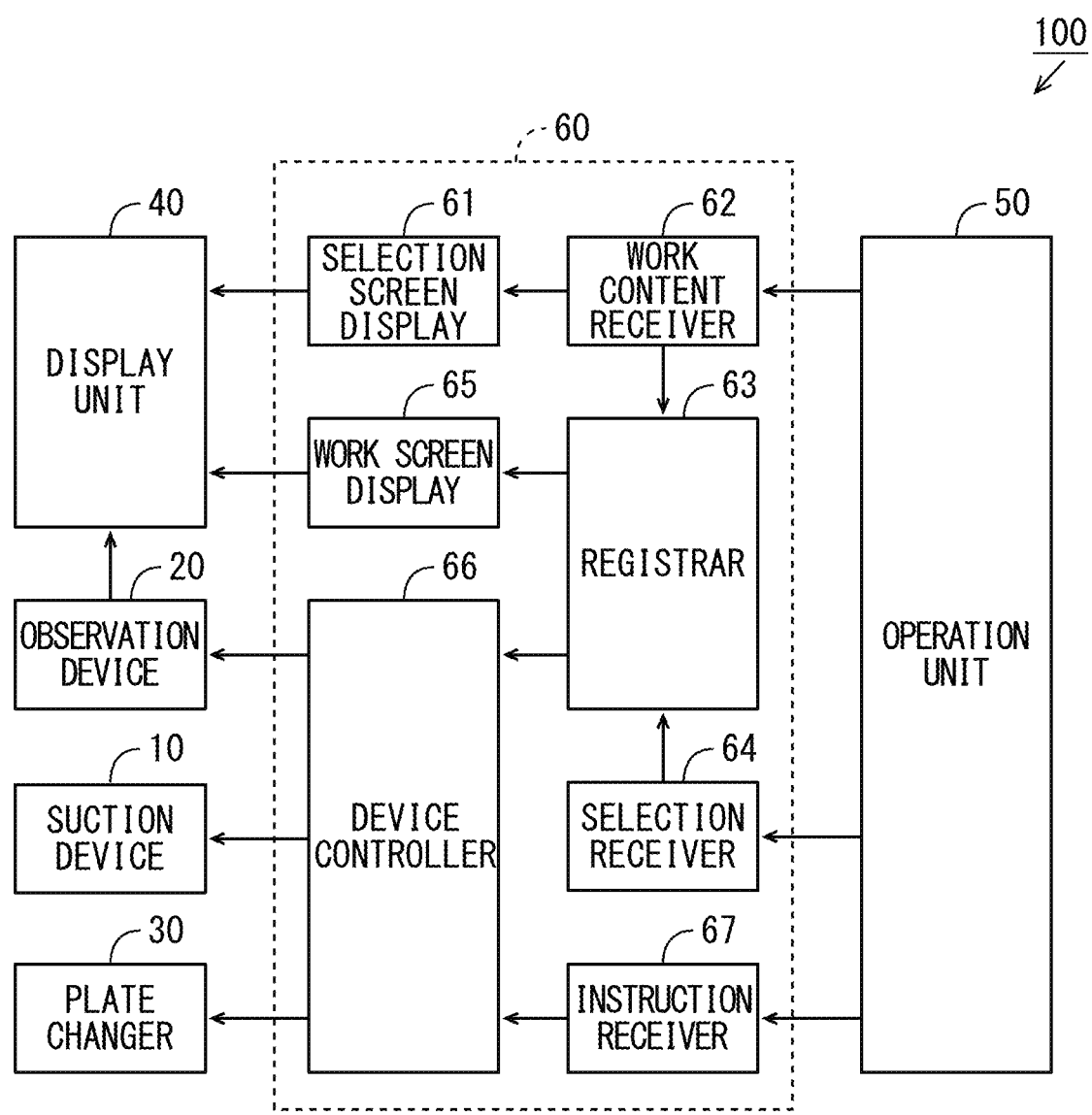
FIG. 10 is a diagram showing the configuration of a controller of FIG. 1.

FIG. 10 is a diagram showing the configuration of the controller 60 of FIG. 1. As shown in FIG. 10, the controller 60 includes a selection screen display 61, a work content receiver 62, a registrar 63, a selection receiver 64, a work screen display 65, a device controller 66 and an instruction receiver 67 as functions. Functions of the controller 60 are implemented by execution of a cell accommodating program stored in the memory by the CPU of the controller 60. Part or all of the functions of the controller 60 may be implemented by hardware such as an electronic circuit.

The selection screen display 61 displays a selection screen such as the method selection screen 41 in the display unit 40. In this case, the selection screen display 61 is an example of a display controller. The work content receiver 62 receives selection of work contents of the suction device 10, the observation device 20 and the plate changer 30 from the operation unit 50 via a selection screen displayed in the display unit 40. Further, the selection screen display 61 switches the selection screen displayed in the display unit 40 in response to reception of work contents by the work content receiver 62.

The registrar 63 registers a method including a plurality of work contents received by the work content receiver 62. The selection receiver 64 receives selection of a method from the operation unit 50 via the method selection screen 41 displayed in the display unit 40. The work screen display 65 displays a work screen 48 corresponding to the method selected by the selection receiver 64 in the display unit 40. The work screen 48 includes an image to be observed by the microscope 24 of the observation device 20.

The device controller 66 controls the work of the suction device 10, the observation device 20 and the plate changer 30 in accordance with a method selected by the selection receiver 64. The instruction receiver 67 receives an instruction for operating the tip position adjustment button 48a, the picking button 48b or the like from the operation unit 50 via the work screen display 65. In this case, the instruction receiver 67 is an example of a scraping instruction receiver. In a case in which the instruction receiver 67 receives an operation instruction, the device controller 66 further controls the work of the suction device 10, the observation device 20 or the plate changer 30 in accordance with the instruction.

(5) Control Process

Figure 11:
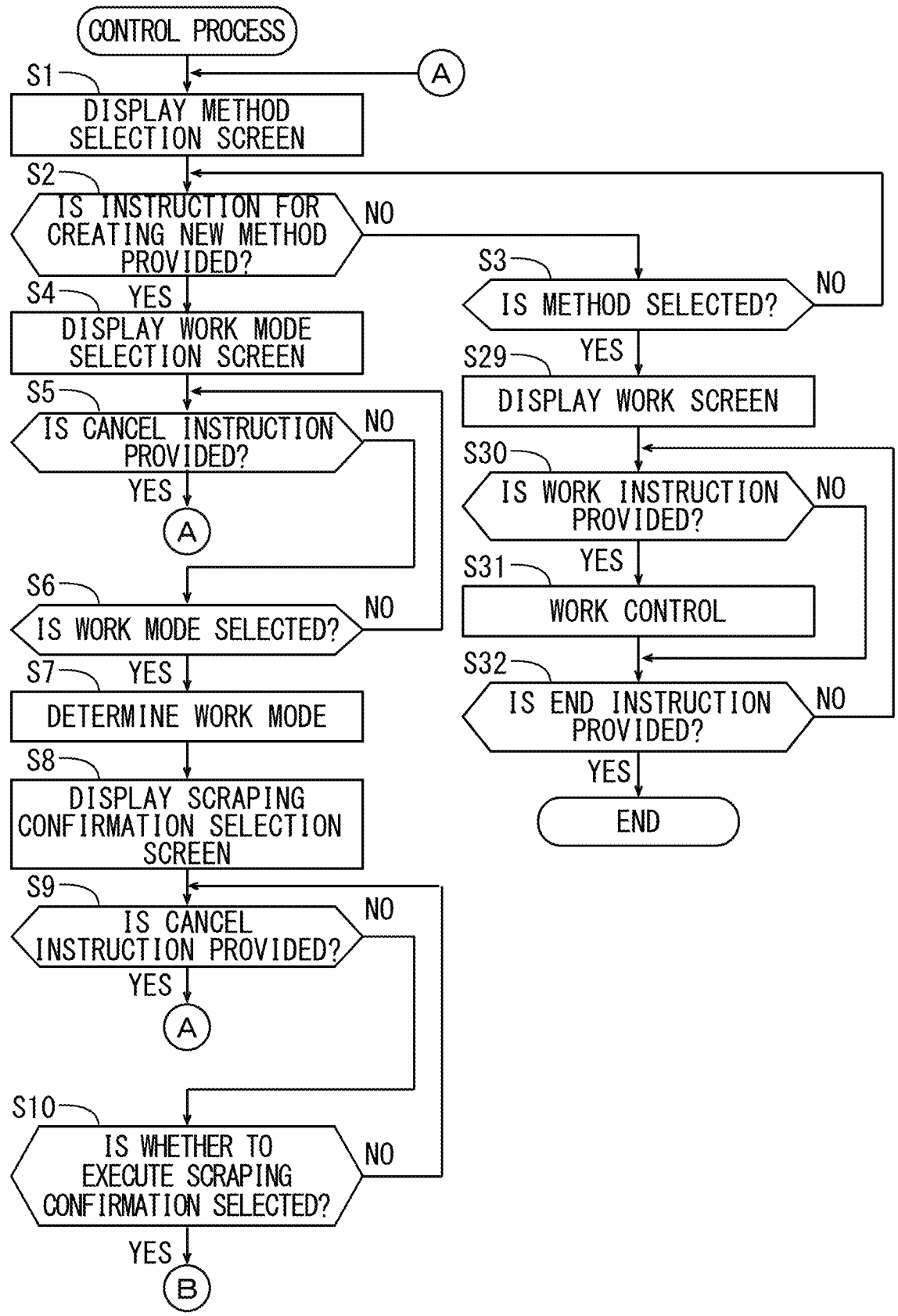
FIG. 11 is a flowchart showing one example of the algorithm of a control process of the cell picking device executed by the controller of FIG. 10.
Figure 12:
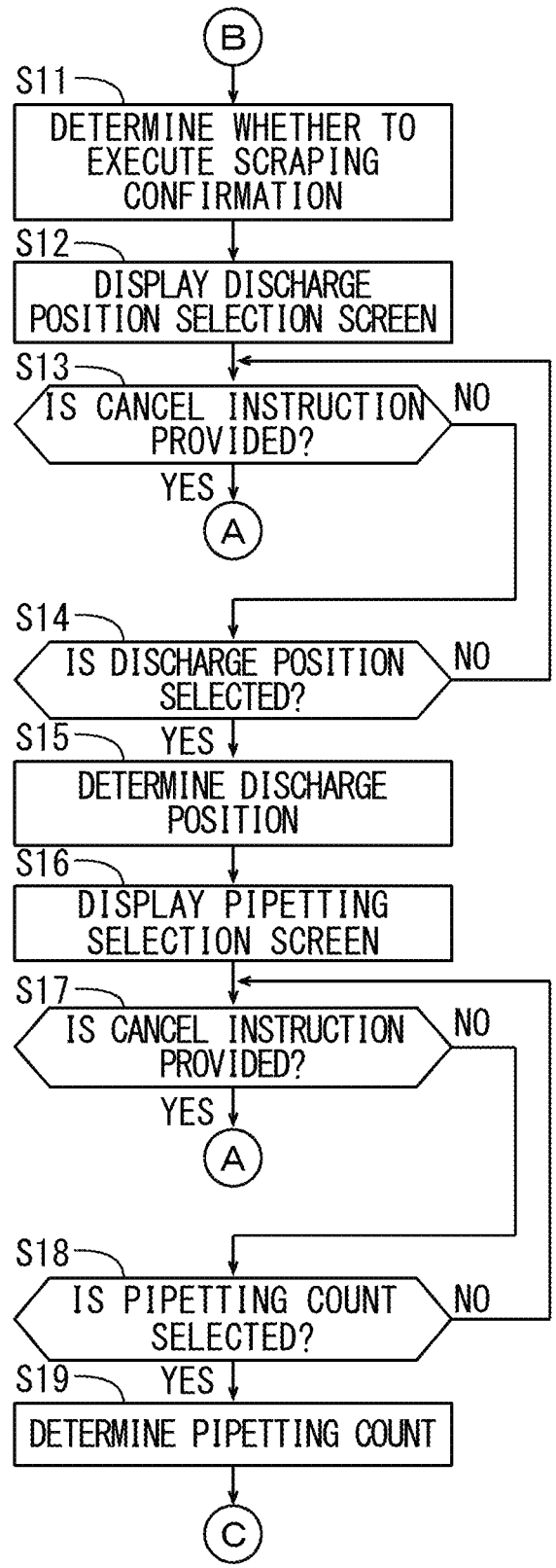
FIG. 12 is a flowchart showing one example of the algorithm of the control process of the cell picking device executed by the controller of FIG. 10.
Figure 13:
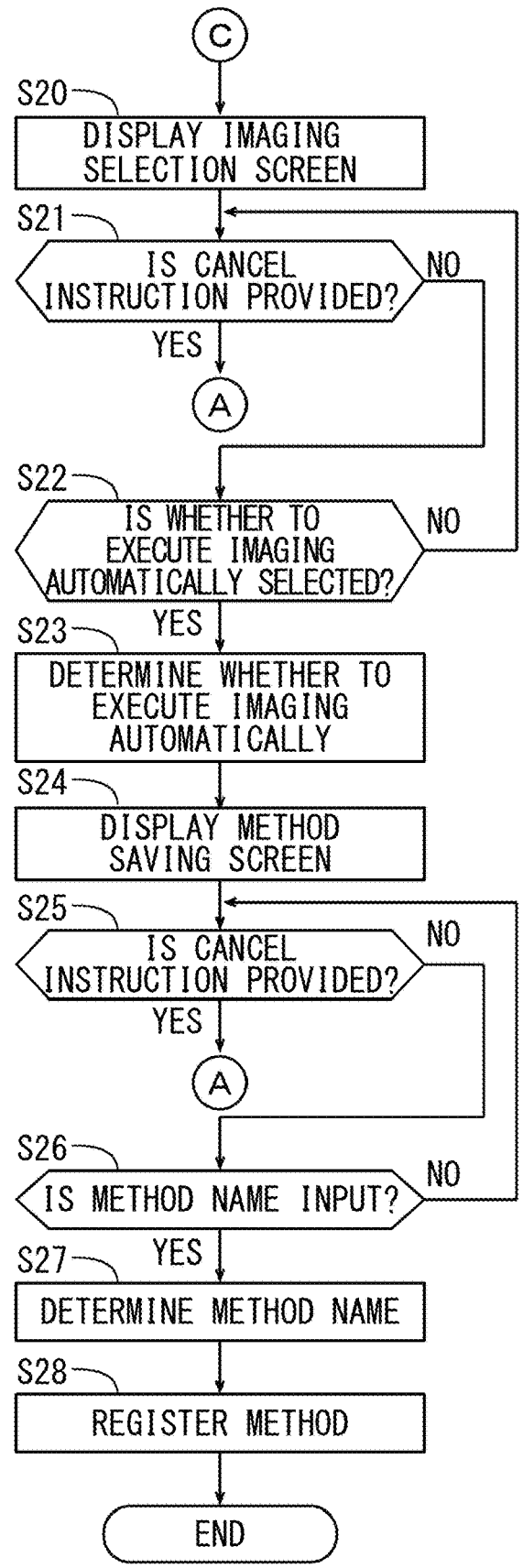
FIG. 13 is a flowchart showing one example of the algorithm of the control process of the cell picking device executed by the controller of FIG. 10.

FIGS. 11 to 13 are flowcharts showing one example of the algorithm of a control process of the cell picking device 100 executed by the controller 60 of FIG. 10. First, the selection screen display 61 displays the method selection screen 41 of FIG. 2 in the display unit 40 (step S1). Next, the work content receiver 62 determines whether an instruction for creating a new method has been provided (step S2). The user can provide an instruction for creating a new method by operating a method selection button 41a in which a method name is not displayed and then operating the start button 41b in the method selection screen 41.

In a case in which an instruction for creating a new method is not provided, the selection receiver 64 determines whether a method has been selected (step S3). The user can select a method by operating a method selection button 41a in which a method name is displayed and then operating the start button 41b in the method selection screen 41. In a case in which a method is not selected, the selection receiver 64 returns to the step S2. The steps S2 and S3 are repeated until an instruction for creating a new method is provided or a method is selected.

In a case in which an instruction for creating a new method is provided in the step S2, the selection screen display 61 displays the work mode selection screen 42 of FIG. 3 in the display unit 40 (step S4). Next, the work content receiver 62 determines whether a cancel instruction has been provided (step S5). The user can provide a cancel instruction by operating the cancel button 4. The same applies to the steps S9, S13, S17, S21 and S25, described below.

In a case in which a cancel instruction is not provided, the work content receiver 62 determines whether a work mode has been selected (step S6). The user can select the picking mode or the removal mode as a work mode by operating the picking mode button 42a or the removal mode button 42b in the work mode selection screen 42.

In a case in which a work mode is not selected, the work content receiver 62 returns to the step S5. The steps S5 and S6 are repeated until a work mode is selected or a cancel instruction is provided. In a case in which a work mode is selected, the work content receiver 62 determines the work mode (step S7). Thereafter, the selection screen display 61 displays the scraping confirmation selection screen 43 of FIG. 4 in the display unit 40 (step S8). Next, the work content receiver 62 determines whether a cancel instruction has been provided (step S9).

In a case in which a cancel instruction is not provided, the work content receiver 62 determines whether execution of scraping confirmation has been selected (step S10). The user can select whether to execute scraping confirmation by operating the YES button 43a or the NO button 43b in the scraping confirmation selection screen 43.

In a case in which whether to execute scraping confirmation is not selected, the work content receiver 62 returns to the step S9. The steps S9 and S10 are repeated until whether to execute scraping confirmation is selected or a cancel instruction is provided. In a case in which whether to execute scraping confirmation is selected, the work content receiver 62 determines whether to execute scraping confirmation (step S11). Thereafter, the selection screen display 61 displays the discharge position selection screen 44 of FIG. 5 in the display unit 40 (step S12). Next, the work content receiver 62 determines whether a cancel instruction has been provided (step S13).

In a case in which a cancel instruction is not provided, the work content receiver 62 determines whether a discharge position has been selected (step S14). The user can select in-view as a discharge position by operating the in-view button 44a and then operating the OK button 44c in the discharge position selection screen 44. Alternatively, the user can select out-of-view as a discharge position by operating the out-of-view button 44b and selecting the identification information of the accommodating plate 120 from the pull-down menu 44d and then operating the OK button 44c in the discharge position selection screen 44.

In a case in which a discharge position is not selected, the work content receiver 62 returns to the step S13. The steps S13 and S14 are repeated until a discharge position is selected or a cancel instruction is provided. In a case in which a discharge position is selected, the work content receiver 62 determines the discharge position (step S15). Thereafter, the selection screen display 61 displays the pipetting selection screen 45 of FIG. 6 in the display unit 40 (step S16). Next, the work content receiver 62 determines whether a cancel instruction has been provided (step S17).

In a case in which a cancel instruction is not provided, the work content receiver 62 determines whether a pipetting count has been selected (step S18). The user can select a pipetting count by selecting a numeral representing the pipetting count from the pull-down menu 45a and then operating the OK button 45b in the pipetting selection screen 45.

In a case in which a pipetting count is not selected, the work content receiver 62 returns to the step S17. The steps S17 and S18 are repeated until a pipetting count is selected or a cancel instruction is provided. In a case in which a pipetting count is selected, the work content receiver 62 determines the pipetting count (step S19). Thereafter, the selection screen display 61 displays the imaging selection screen 46 of FIG. 7 in the display unit 40 (step S20). Next, the work content receiver 62 determines whether a cancel instruction has been provided (step S21).

In a case in which a cancel instruction is not provided, the work content receiver 62 determines whether to automatically execute imaging has been selected (step S22). The user can select to automatically execute imaging by operating the pre-and-post suction button 46a or the post-suction button 46b in the imaging selection screen 46. Alternatively, the user can select not to automatically execute imaging by operating the NO button 46c in the imaging selection screen 46.

In a case in which whether to automatically execute imaging is not selected, the work content receiver 62 returns to the step S21. The steps S21 and S22 are repeated until whether to automatically execute imaging is selected or a cancel instruction is provided.

In a case in which whether to automatically execute imaging is selected, the work content receiver 62 determines whether to execute imaging automatically (step S23). Thereafter, the selection screen display 61 displays the method saving screen 47 of FIG. 8 in the display unit 40 (step S24). Next, the work content receiver 62 determines whether a cancel instruction has been provided (step S25).

In a case in which a cancel instruction is not provided, the work content receiver 62 determines whether a method name has been input (step S26). The user can input a method name by inputting a character string representing the method name in the method name input field 47*a* and then operating the save button 47*b* in the method saving screen 47.

In a case in which the method name is not input, the work content receiver 62 returns to the step S25. The steps S25 and S26 are repeated until a method name is input or a cancel instruction is provided. In a case in which a method name is input, the work content receiver 62 determines the method name (step S27). Thereafter, the registrar 63 creates and registers a method based on the work contents determined in the steps S7, S11, S15, S19 and S23 and the method name determined in the step S27 (step S28). Thereafter, the registrar 63 ends the control process of the cell picking device 100.

In a case in which a cancel instruction is provided in the steps S9, S13, S17, S21 and S25, the selection screen display 61 returns to the step S1. In this case, the method selection screen 41 of FIG. 2 is displayed in the display unit 40.

In a case in which a method is selected in the step S3, the work screen display 65 displays the work screen 48 of FIG. 9 corresponding to the selected method in the display unit 40 (step S29). Next, the instruction receiver 67 determines whether an instruction in regard to work of the cell picking device 100 has been received (step S30). The user can provide an instruction in regard to work of the cell picking device 100 by operating the tip position adjustment button 48*a*, the picking button 48*b* or the like in the work screen 48. In a case in which an instruction in regard to work of the cell picking device 100 is not received, the instruction receiver 67 proceeds to the step S32.

In a case in which an instruction in regard to work of the cell picking device 100 is received, the device controller 66 controls the work of the cell picking device 100 based on a selected method and a received instruction (step S31) and proceeds to the step S32. In the step S32, the instruction receiver 67 determines whether an end instruction has been received (step S32). The user can provide an end instruction by performing a predetermined operation in the work screen 48.

In a case in which an end instruction is not provided, the instruction receiver 67 returns to the step S30. The steps S30 to S32 are repeated until an instruction in regard to work of the cell picking device 100 is received or an end instruction is received. In a case in which an end instruction is received, the instruction receiver 67 ends the control process of the cell picking device 100.

(6) Effects

In the cell picking device 100 according to the present embodiment, the imager 23 is provided so as to be able to pick up an image of a sample in the sample container 110 placed on the stage 21. The driver 16 is provided such that the sample scraping work and the sample sucking work are executed by the tip 12 attached to the sucker 11.

In a case in which selection of the work contents of the drivers 16, 34 and the imager 23 is received by the work content receiver 62, a method including the received work contents of the drivers 16, 34 and the imager 23 is registered by the registrar 63. The device controller 66 controls the work of the drivers 16, 34 and the imager 23 in accordance with the registered method.

With this configuration, a work procedure suitable for a user request can be registered. Therefore, even in a case in which not being skilled, the user can cause the cell picking device 100 to work in accordance with desired work contents and a registered work procedure. Thus, operability of the cell picking device 100 can be improved.

(7) Other Embodiments (a) While the selection screens of FIGS. 2 to 8 are sequentially displayed in the display unit 40 in the above-mentioned embodiment, the embodiment is not limited to this. One or all of the selection screens out of the selection screens of FIGS. 2 to 8 may be displayed in the display unit 40 at the same time.

Further, part of the selection screens of FIGS. 2 to 8 may be configured not to be displayed. For example, the suction device 10 may work only in the picking mode and does not have to work in the removal mode. In this case, the work mode selection screen 42 of FIG. 3 is not displayed. Alternatively, the observation device 20 does not have to include the imager 23. In this case, the imaging selection screen 46 of FIG. 7 is not displayed.

(b) While the work contents of the suction device 10, the observation device 20 and the plate changer 30 are selected via the GUI in the above-mentioned embodiment, the embodiment is not limited to this. The work content may be selected via another user interface such as a CUI (Character User Interface).

(8) Aspects

It is understood by those skilled in the art that the plurality of above-mentioned illustrative embodiments are specific examples of the below-mentioned aspects.

(Item 1) A cell picking device according to one aspect for sucking cells from a liquid sample in a sample container, may include a stage on which the sample container is placeable, a sucker to which a pipette tip is attachable, a driver that drives the sucker to execute sample scraping work and drives the sucker to execute sample sucking work, using the pipette tip, a work content receiver that receives selection of work contents of the driver, a registrar that registers a work procedure including work contents of the driver received by the work content receiver, and a device controller that controls work of the driver in accordance with a work procedure registered by the registrar.

In this cell picking device, the driver is provided such that the sample scraping work and the sample sucking work are executed by the pipette tip attached to the sucker. In a case in which the selection of the work contents of the driver is received by the work content receiver, the work procedure including the received work contents of the driver is registered by the registrar. The work of the driver is controlled by the device controller in accordance with the registered work procedure.

With this configuration, the work procedure suitable for a user request can be registered. Therefore, even in a case in which not being skilled, the user can cause the cell picking device to work in accordance with desired work contents and a registered work procedure. Thus, operability of the cell picking device can be improved.

(Item 2) The cell picking device according to item 1, wherein the work content receiver may be configured to be capable of receiving selection of a plurality of work contents of the driver, the registrar may be configured to be capable of registering a plurality of work procedures based on a plurality of work contents of the driver received by the work contents receiver, the cell picking device may further include a selection receiver that receives selection of any work procedure out of a plurality of work procedures registered by the registrar, and the device controller may control work of the driver in accordance with a work procedure received by the selection receiver.

In this case, a plurality of work procedures can be registered. Therefore, the user can select a desired work procedure from among a plurality of registered procedures and cause the cell picking device 100 to work in accordance with the selected work procedure. Thus, operability of the cell picking device can be improved more sufficiently.

(Item 3) The cell picking device according to item 1 or 2, wherein the selection of work contents of the driver may include selection of picking in which a sample in the sample container is sucked into the pipette tip and the sucked sample is discharged into an accommodating plate and removal in which a sample in the sample container is sucked into the pipette tip to be removed.

In this case, the user can easily discharge cells in a sample by selecting picking. Further, the user can easily remove cells in a sample by selecting removal.

(Item 4) The cell picking device according to item 1 or 2, may further include a scraping instruction receiver that receives an instruction for the scraping work, wherein the selection of work contents of the driver may include selection of whether to execute sample scraping confirmation, the driver, in a case in which execution of scraping confirmation in a work procedure is selected, may drive the sucker to execute the scraping work in response to an instruction provided by the scraping instruction receiver and then stops driving the sucker, and in a case in which non-execution of scraping confirmation in a work procedure is selected, may drive the sucker to execute the scraping work in response to an instruction provided by the scraping instruction receiver and then drives the sucker to execute the sucking work.

With this configuration, the user can reliably suck cells even in a case in which the cells are relatively large by selecting execution of scraping confirmation in a work procedure. Further, the user can end the work in a short period of time by selecting not to execute scraping confirmation in the operation procedure.

(Item 5) The cell picking device according to item 1 or 2, wherein the selection of work contents of the driver may include selection of a discharge position to which a sample is discharged by the pipette tip, and the discharge position may include in-view and out-of-view of the microscope.

In this case, the user can observe suction and discharging of cells using the microscope by selecting in-view of the microscope as a sample discharge position. Further, the user can discharge cells to a desired accommodating plate by selecting out-of-view of the microscope as a sample discharge position.

(Item 6) The cell picking device according to item 1 or 2, wherein the selection of work contents of the driver may include selection of a count of sample pipetting by the pipette tip.

In this case, the user can separate a mass of cells and level the cells to a desired extent by selecting a pipetting count.

(Item 7) The cell picking device according to item 1 or 2, wherein the selection of work contents of the driver may include selection of a sample sucking capacity.

In this case, the user can execute sucking work more efficiently by selecting a sample sucking capacity.

(Item 8) The cell picking device according to item 1 or 2, wherein the selection of work contents of the driver may include selection of a sample sucking speed and/or a moving speed of the pipette tip.

In this case, the user can execute sucking work more efficiently by selecting a cell sucking speed and/or a moving speed of the pipette tip.

(Item 9) The cell picking device according to item 1 or 2, may further include an imager provided to be capable of picking up an image of a sample in the sample container placed on the stage, wherein the work contents receiver may further receive selection of work contents of the imager, the registrar may register a work procedure further including work contents of the imager received by the work content receiver, the device controller may further control work of the imager in accordance with a work procedure registered by the registrar, the selection of work contents of the imager may include selection of whether to execute imaging automatically, and the imager may acquire an image representing whether a sample has been sucked by the pipette tip in a case in which execution of imaging in a work procedure is selected.

In this case, the user can confirm whether a sample has been sucked using an image by selecting execution of automatic imaging in a work procedure. Further, the user can end work in a short period of time by selecting not to execute automatic imaging in the work procedure.

(Item 10) The cell picking device according to item 1 or 2, may further include a display controller that displays choices of work contents of the driver in a display unit using a graphical user interface.

In this case, the user can easily select the work contents via a graphical user interface displayed in the display unit.

The invention claimed is:
1. A cell picking device for sucking cells from a liquid sample in a sample container, comprising:
 a stage on which the sample container is placeable;
 a sucker to which a pipette tip is attachable;
 a driver that drives the sucker to execute sample scraping work and drives the sucker to execute sample sucking work, using the pipette tip
 a display; and
 a device controller configured to:
 display on the display a plurality of work contents of the driver that perform a different work procedure on a single screen;
 determine work contents every time the device controller receives selection of work contents of the driver, from the screen that includes a step display region and a GUI display region for receiving the selection of the work contents of the driver that corresponds to a work step selected from the plurality of work steps, the work contents indicating an operation executed by the driver, registers a work procedure including the determined work contents of the driver, wherein the step display region includes icons for a scaping confirmation, discharge position, pipetting, imaging and method saving; and
 control work of the driver in accordance with the registered work procedure;
 receive an instruction for the scraping work determine work contents every time the device controller receives selection of work contents of the driver;

wherein the selection of work contents of the driver includes selection of whether to execute confirmation that the scraping work has been performed;

the driver, based on execution of the confirmation in a work procedure being selected, drives the sucker to execute the scraping work in response to an instruction provided by the device controller and then stops driving the sucker, and based on non-execution of the confirmation in a work procedure being selected, drives the sucker to execute the scraping work in response to an instruction provided by the device controller and then drives the sucker to execute the sucking work.

2. The cell picking device according to claim 1, wherein the device controller is further configured to:

register of a plurality of work procedures based on the received plurality of work contents of the driver, receive selection of any work procedure of the plurality of work procedures procedure out of the registered plurality of work procedures, and control work of the driver in accordance with the received work procedure.

3. The cell picking device according to claim 1, wherein the selection of work contents of the driver includes selection of picking in which a sample in the sample container is sucked into the pipette tip and the sucked sample is discharged into an accommodating plate and removal in which a sample in the sample container is sucked into the pipette tip to be removed.

4. The cell picking device according to claim 1, wherein the selection of work contents of the driver includes selection of a discharge position to which a sample is discharged by the pipette tip, and the discharge position includes in-view and out-of-view of the microscope.

5. The cell picking device according to claim 1, wherein the selection of work contents of the driver includes selection of a count that the pipette tip pipets a sample.

6. The cell picking device according to claim 1, wherein the selection of work contents of the driver includes selection of a sample sucking capacity.

7. The cell picking device according to claim 1, wherein the selection of work contents of the driver includes selection of a sample sucking speed and/or a moving speed of the pipette tip.

8. The cell picking device according to claim 1, further comprising an imager configured to pick up an image of a sample in the sample container placed on the stage, wherein the device controller further receives selection of work contents of the imager, registers a work procedure further including the received work contents of the imager, further controls work of the imager in accordance with the registered work procedure, the selection of work contents of the imager includes selection of whether to execute imaging automatically, and the imager acquires an image representing whether a sample has been sucked by the pipette tip in a case in which execution of imaging in a work procedure is selected.

* * * * *